United States Patent [19]

Brown

[11] Patent Number: 5,047,061
[45] Date of Patent: Sep. 10, 1991

[54] PROSTHESIS HOLDER

[76] Inventor: Byron L. Brown, 2315 Hendricks, Fort Smith, Ark. 72903

[21] Appl. No.: 300,345

[22] Filed: Jan. 20, 1989

[51] Int. Cl.5 ............................ A61F 2/32; A61F 5/04
[52] U.S. Cl. .......................................... 623/23; 606/92
[58] Field of Search ........................ 623/16, 18, 19, 20, 623/22, 23; 128/92; 606/90-94

[56] References Cited

U.S. PATENT DOCUMENTS

| | | | |
|---|---|---|---|
| Re. 28,895 | 7/1976 | Noiles | 623/22 |
| 3,698,017 | 10/1972 | Scales et al. | 623/22 |
| 4,357,716 | 11/1962 | Brown | 623/23 |
| 4,718,909 | 1/1988 | Brown | 623/18 |

Primary Examiner—David J. Isabella
Attorney, Agent, or Firm—Sigalos, Levine & Montgomery

[57] ABSTRACT

An improved prosthesis holder for retaining a prosthesis in the desired position with respect to the femoral canal of a femur during surgery. The holder comprises a holding unit member specially adapted for positioning in cooperative association with the neck of the prosthesis so as to provide improved holding, protective and positioning characteristics to the holder.

3 Claims, 7 Drawing Sheets

PROSTHESIS HOLDER

BACKGROUND OF THE INVENTION

The present invention relates to a method and apparatus for positioning a femoral stem hip prosthesis in a femoral canal with the use of a cement.

It is well known in the prior art to initiate total hip replacement as disclosed in U.S. Pat. Nos. 4,357,716, granted Nov. 9, 1982, and 4,718,909, granted Jan. 12, 1988. As described in these patents, the femur is prepared to receive a femoral stem prosthesis which has a head, neck and stem. The proximal end of the femur is prepared by resecting the head and neck of the femur and then reaming and possibly rasping or curetting the intramedullary canal. Once the canal has been properly prepared by reaming and curettage, the distal canal is plugged, utilizing a bone plug obtained from the femoral head or formed in any other of the well known alternate methods. In any event, the plug effectively seals off the canal to prevent excessive penetration of cement below the tip of the stem of the prosthesis. Positioning of the prosthesis stem in the femoral canal and the relationship of the head and neck of the prosthesis with the shaft of the femur is important and is related in part to the position of the distal end of the femoral stem as well as the position of the proximal end of the prosthesis stem in the intertrochanteric area.

As described in U.S. Pat. No. 4,357,716, a fixed device or apparatus holds the prosthesis in fixed relationship to the femur thus eliminating motion of the prosthesis during the time that the pressurized cement is applied about the prosthesis stem in the femoral canal, and the pressure is maintained until the cement hardens.

The proposals of the above-identified patent have been efficacious in contributing to the successful implantation of prostheses in which the stems and heads are formed integrally. However, there have more recently been proposed prostheses in which the heads can be and in fact are separated from the remainder of the prostheses. Such separation feature makes it possible for the stem of a prosthesis to be handled more easily than if the head were permanently attached and it also makes possible the mounting of heads to optimally fit the prosthesis to the particular characteristics of the patient.

As is known to those skilled in the art, the heads of hip replacement prostheses must be machined to extraordinarily high tolerances and finely polished so as to provide surfaces adapted for relative movement as is occasioned when a patient walks after the prosthesis has been installed and healing has occurred. Even the slightest nick on such a highly machined head can render the entire device inoperative and it must then be discarded. Since prostheses are relatively expensive, it will be evident that the removability of the head constitutes a significant improvement, at least in some instances; and, consequently, prostheses having removable heads have become increasingly attractive.

As described with respect to the above-identified patents, a feature of the previously proposed apparatus or devices made use of the neck of the prosthesis (the portion adjacent to the head) for the purpose of holding the proximal end of the prosthesis in position while cementing was occurring. However, with the removable head feature, most necks are no longer suitable for this purpose. Moreover, according to the prior art proposals, utilization of the neck portion of the prosthesis for holding resulted in a relatively small degree of adjustability, thereby in some instances unduly restricting the adjustment needed by the surgeon. In addition, when a stem prosthesis with a removable head is implanted, there continues to be a need to protect the finely machined neck. Accordingly, there has continued to be a need for an improved versatile device or apparatus which is adapted for use with both removable and fixed head prostheses.

OBJECTS AND FEATURES

It is one general object of this invention to improve medical prosthesis holding devices.

It is another object of the invention to provide holding devices that are adaptable for holding different types of prostheses (e.g., those with fixed or removable heads).

It is yet another object of the invention to provide a holding device which features an increased range of adjustability for the prosthesis being held in position.

It is still another object of the invention to provide holding units adapted for holding and protecting prosthesis necks of different geometrical shapes.

It is yet one further object of the invention to provide a unit for mounting about the prosthesis neck which effectively holds the proximal end of a prosthesis in the desired position while providing an improved range of adjustability.

Accordingly, in accordance with one feature of the invention, a unit is temporarily positioned on the proximal end of the neck of a removable head prosthesis, thereby protecting the surfaces of the neck while simultaneously providing for positioning and adjustment.

In accordance with another feature of the invention, the collar is of essentially uniform outer lateral geometry thereby rendering the holding unit compatible with an associated device or apparatus.

In accordance with one other feature of the invention, the interior geometries of the holding units are adapted to fit corresponding outer geometries of the necks of various prostheses, thereby providing usability with a wide variety of prostheses.

In accordance with yet another feature of the invention, prosthesis necks of bulbous or other hard-to-fit geometries are accommodated by the utilization of holding units having form-fit inner geometries and a full or partial slit in the wall thereof, thereby providing for easy mounting while retaining excellent holding and positioning characteristics.

In accordance with still one other feature of the invention, the holding units optionally may be made of material such as a silicone elastomer that exhibits a substantial amount of holding friction while being smooth and protective of the critical surfaces of the necks of the prosthesis, or they may be made of metal or moderately firm plastic and may be lined with silicone elastomer.

In accordance with yet one other feature of the invention, for prostheses having non-detachable heads, provision is made for using holding units that are divided vertically into two parts, thereby facilitating their mounting on the prostheses necks.

In accordance with still one other feature of the invention, in one alternative embodiment, the holding unit is multi-sectioned, and a thin arcuate split ring is provided for retaining the plurality of sections in position on the desired surface of the prosthesis, thereby facilitating mounting and use thereof. In addition, the sections may be attached by a pin or bolt connecting the sections near their proximal ends.

These and other objects and features will be apparent from the following description, by way of preferred embodiments, with reference to the drawing.

DETAILED DESCRIPTION OF INVENTION

Figure 1:
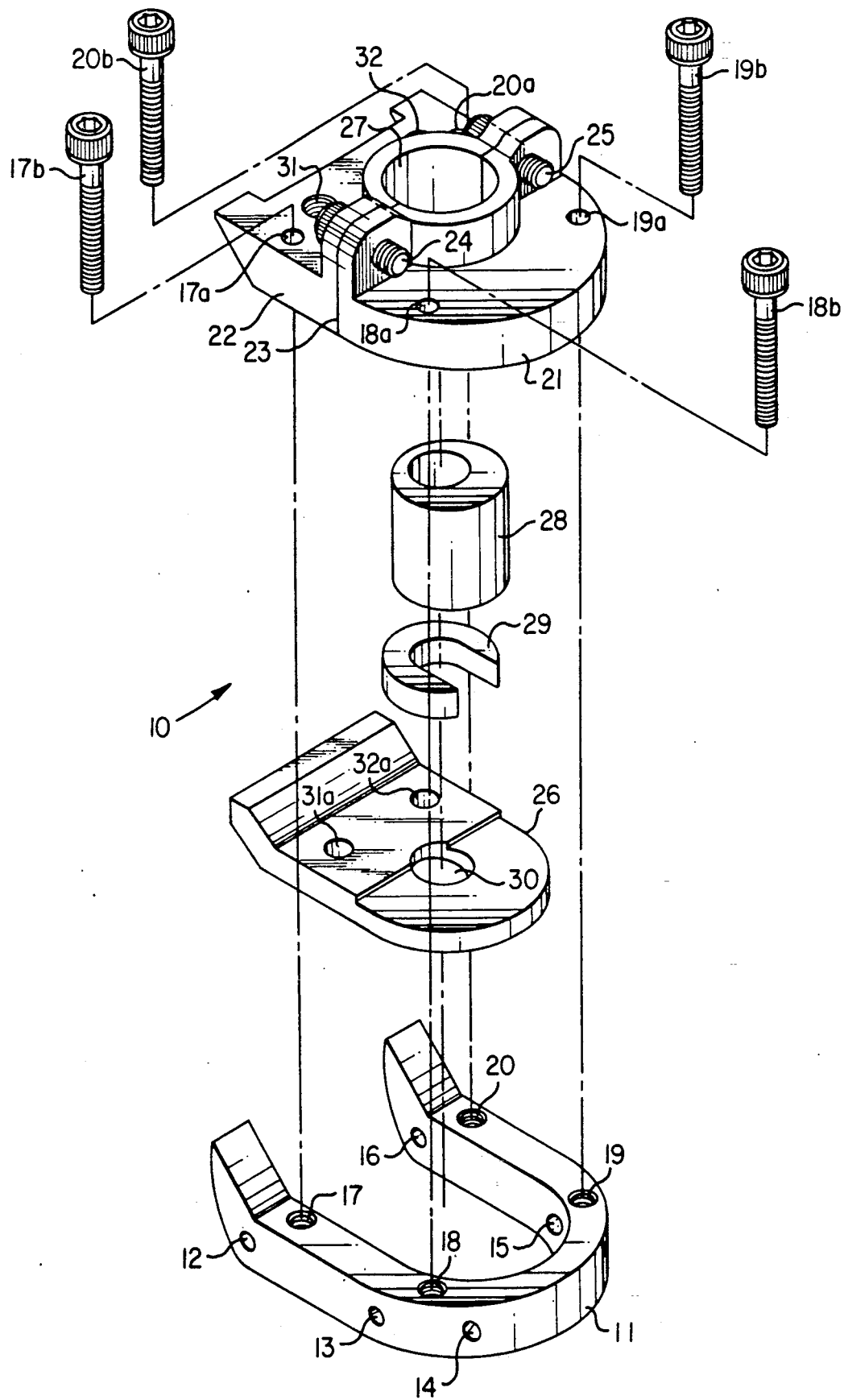
FIG. 1 is an exploded perspective view of the device for cementing a hip prosthesis in a femoral canal according to the inventive concepts hereof.

Now turning to the drawing, and more particularly FIG. 1 thereof, it will be observed that there is depicted a prosthesis holding device 10 having some similarity to that depicted in FIG. 1 of co-pending U.S. Pat. application Ser. No. 077,177, which was filed Jul. 24, 1987, and entitled "Improved Drill Bit Guide." The disclosure of that application is incorporated herein and made a part hereof.

The device 10 of the present invention is shown in FIG. 1 of the present specification. FIG. 1 includes base guide 11 which is generally U-shaped and is described in detail in the above-referenced co-pending application. It includes orifices such as those shown at 12–16 in which drill bit sleeves (not shown) are inserted. Also within base guide 11 are four drilled and tapped apertures 17–20 which are positioned for registration with aligned apertures 17a–20a in ceiling halves 21 and 22. As will be observed from reference to the upper portion of FIG. 1, ceiling halves 21 and 22 are removably joined along line 23 and bolted together by threaded fastening members 24 and 25. Triple threaded bolts 17b–20b provide for completing the fastening together of the parts of FIG. 1 in tight assembly.

In addition to the above-described parts, there is the sealer 26. Sealer 26 is preferably constructed of a plastic which is pliable to a moderate degree or may be made of a silicone elastomer. As used herein, the word "plastic" in relation to sealer 26 is inclusive of any of the foregoing materials.

A femoral stem prosthesis with a detachable head (FIGS. 7–11 inclusive), has a polished neck 42 extending upwardly through opening 27 (FIG. 1) between ceiling half 21 and mating half 22. The neck is surrounded by an adjustment ring 28 and/or holding unit 29 and thence downwardly through opening 30 in separator sealer 26.

When a femoral stem prosthesis with a non-detachable head is employed, an adjustment ring such as shown in U.S. Pat. No. 4,357,716 may adequately hold the prosthesis. When an adjustment ring of a tubular or cylindrical design is constructed of somewhat firm material and that adjustment ring is to be used with a femoral stem prosthesis with a non-detached head, it is desirable to divide the holding unit longitudinally into two or more parts (preferably two).

Figure 19:
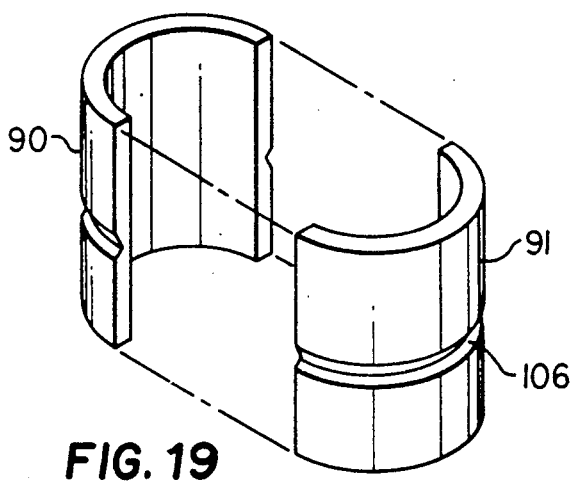
FIG. 19 depicts one form of split collar-like device.
Figure 20:
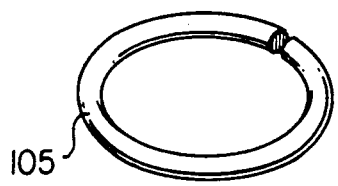
FIG. 20 depicts a split ring for use with the device of FIG. 19.

When a two part adjustment ring (FIG. 19) is employed the process of fitting the adjustment ring around the neck of the prosthesis, properly placing the ceiling and separator sealer can be made easier by the use of the split ring 105 of FIG. 20 which can be snapped around the two parts 90 and 91 of the adjustment unit (FIG. 19).

Figure 3:
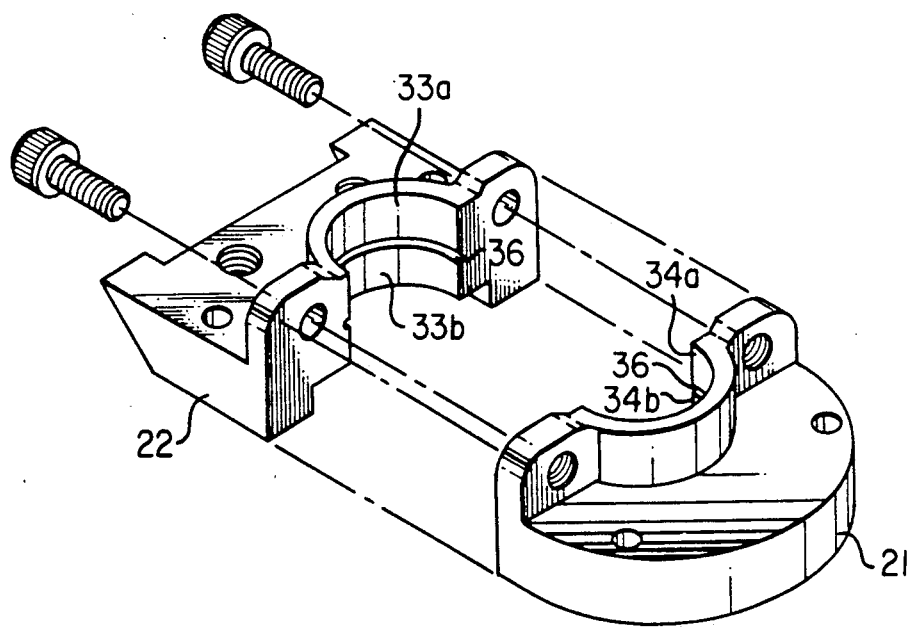
FIG. 3 is a perspective view showing the ceiling portion of the assembly of FIG. 1.

When a split metal ring is used around an adjustment unit, it is desirable to have a circumferencial groove such as groove 106 (FIG. 19) on the exterior of the adjustment unit. The split ring then lies partially within this groove and partially within the groove 36 of the ceiling (FIG. 3).

Furthermore, the positioning of the femoral stem prosthesis with an adjustment unit which is surrounded by a split ring can be accurately fitted in the ceiling by the presence of a groove such as that of groove 36 on the inner aspect of wall of the ceiling which surrounds opening 27.

The split ring and the groove around the adjustment ring and in the ceiling may also be used with tubular like holding units. In essence, as the adjustment ring as shown in U.S. Pat. No. 4,357,716 is used in conjunction with a small U-shaped holding unit such as unit 29 (FIG. 1), there ordinarily is a need for a tubular holding unit. Some such tubular holding units can function to a slight degree as adjustment rings. However, with the manufacturing of multiple sized reamers and rasps and the use of centering devices, the need for major adjustments by the use of adjustment rings has lessened. Furthermore the variety of tubular holding rings may provide for slightly needed adjustment. However, the major function of such tubular holding units is to hold femoral stem prostheses. Accordingly, the term "adjustment unit" includes some such embodiments usually for femoral stems with attached heads, the expression "holding unit" being ordinarily applicable to femoral stems with detachable heads. However with some femoral stems there is used a separate adjustment ring and a separate holding unit. Furthermore, some adjustment rings and some holding units may be more easily used when they are but a single piece with or without a slit, while others may be more easily used when completely divided or a two piece unit.

When an adjustment ring or a holding unit is split vertically and is made of somewhat resilient material it may be spread sufficiently to slip over the irregularities at or below the neck to be positioned and then held more securely by the approximation of the two halves of the ceiling.

Further reference to ceiling half 22 reveals the existence of threaded apertures 31 and 32 which, as described in connection with the aforementioned co-pending application, are provided for the temporary attachment of a syringe mechanism for the injection of prosthesis cementing material. Corresponding apertures 31a and 32a in sealer 26 are seen to be axially aligned with apertures 31 and 32 to provide for the flow of cement therethrough.

Figure 2:
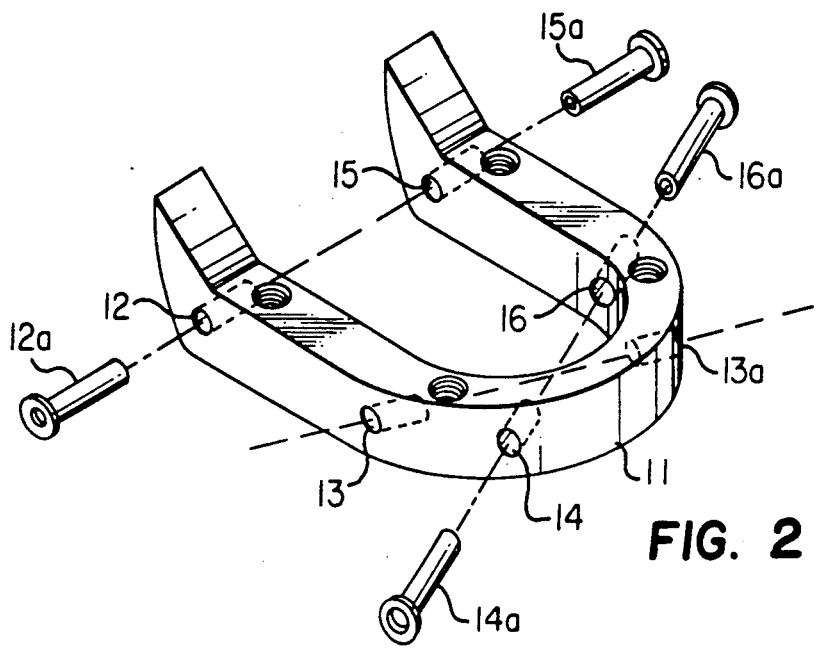
FIG. 2 is a perspective view showing the U-shaped frame portion (hereinafter generally referred to as a base guide) of the assembly of FIG. 1.

Now referring to FIG. 2, U-shaped frame 11 heretofore described as a base guide, is shown in greater detail. Drill bit guides 12a, 14a, 15a and 16a are shown as described in the above-identified co-pending application. Although not shown in FIG. 2, it is contemplated that similar drill bit guides are provided for orifice 13 and juxtaposed orifice 13a.

FIG. 3 shows the ceiling exploded to more clearly depict halves 21 and 22. As will be observed from an inspection of the surfaces that define opening 27 (FIG. 1), such surfaces hereinafter referred to as 33 and 34 respectively, are divided into upper sections 33a and 34a and lower sections 33b and 34b by annular groove 36. Annular groove 36 provides a depression to accept a split metal ring such as ring 105 (FIG. 20).

Figure 4:
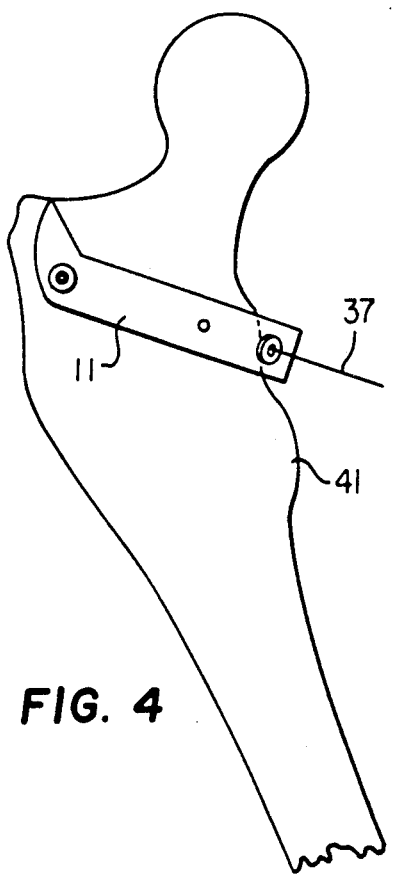
FIG. 4 is a side elevation view of the head, neck and upper part of a typical femur prior to resection and showing the U-shaped frame or base guide of FIG. 2 in position thereon.
Figure 5:
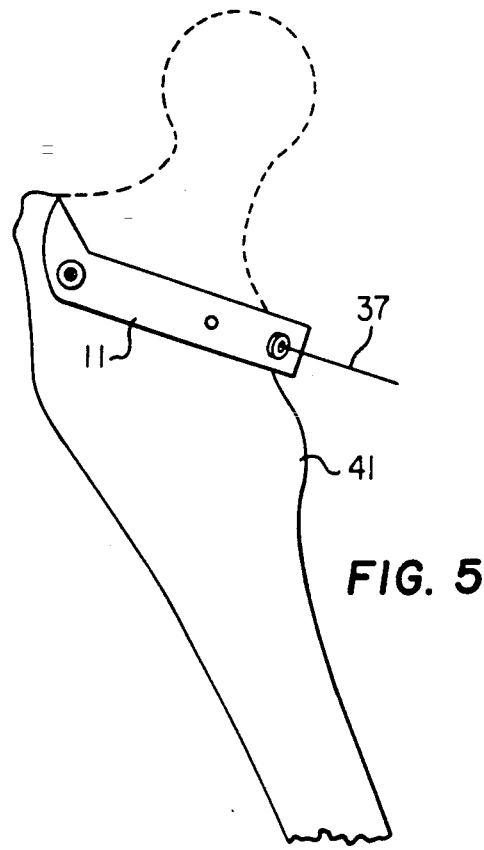
FIG. 5 is a view similar to that of FIG. 4 except showing the resected (removed) part of the femur in dotted line form.

Now turning to FIGS. 4 and 5, it will be seen that they depict the femur 41 with U-shaped base guide 11 in place before and after resectioning of the upper part of the femur. Using the techniques described in that co-pending application, the surgeon positions guide 11 in the appropriate location and proceeds to affix it to the femur by drilling through the bone and inserting pins as represented by line 37. The techniques by which this is accomplished are described in detail in the above-identified co-pending application.

Figure 6:
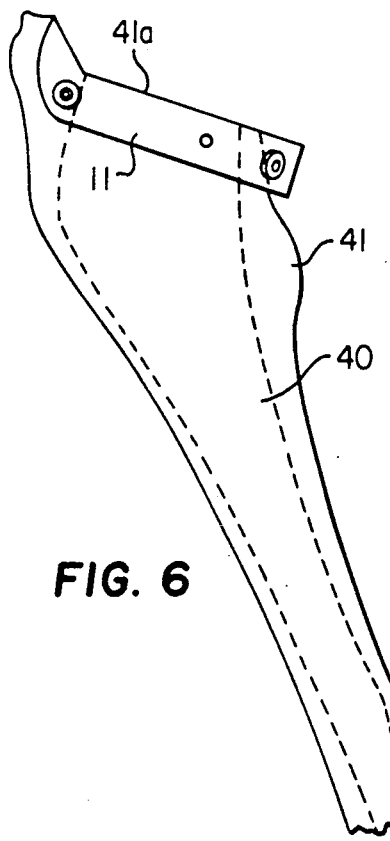
FIG. 6 is a view similar to that of FIG. 5 showing the resected portion entirely omitted and depicting by dashed line the outline of the femoral canal within the femur.

FIG. 6 depicts the femur 41 after resectioning and with the U-shaped base guide 11 affixed thereto by pins (not shown). Line 41a marks both the upper boundary of base guide 11 and the bone surface.

Figure 7:
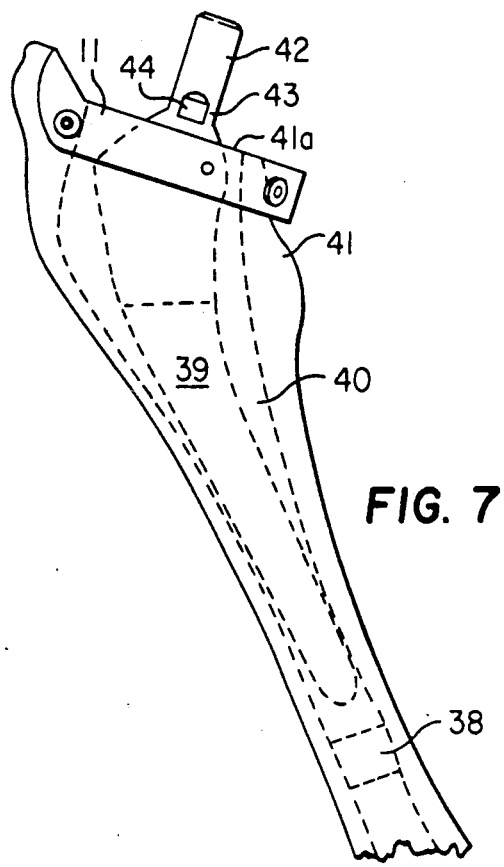
FIG. 7 is a view similar to that of FIG. 6 showing the principal part of a representative prosthesis device inserted within the femoral canal and additionally illustrating the positioning of a plug to prevent migration of any cementing medium downwardly past a predetermined point.

FIG. 7 depicts the resectioned femur as shown in FIG. 6 but with the addition of the bone plug 38 (mentioned above) and the metallic prosthesis member 39 suitably positioned within the interior canal 40 of femur 41.

As is well known to those skilled in the art, metallic prostheses of the type contemplated by the hereindescribed example can take various forms, including those with detachable heads and those that are manufactured as one integral member. Moreover, both the detachable and non-detachable head varieties vary in some significant aspects. Thus, for example, some may include an extending projection such as projection 110 shown in FIG. 21. However, detachable head prostheses such as those illustrated herein have come into very common usage.

Figure 22:
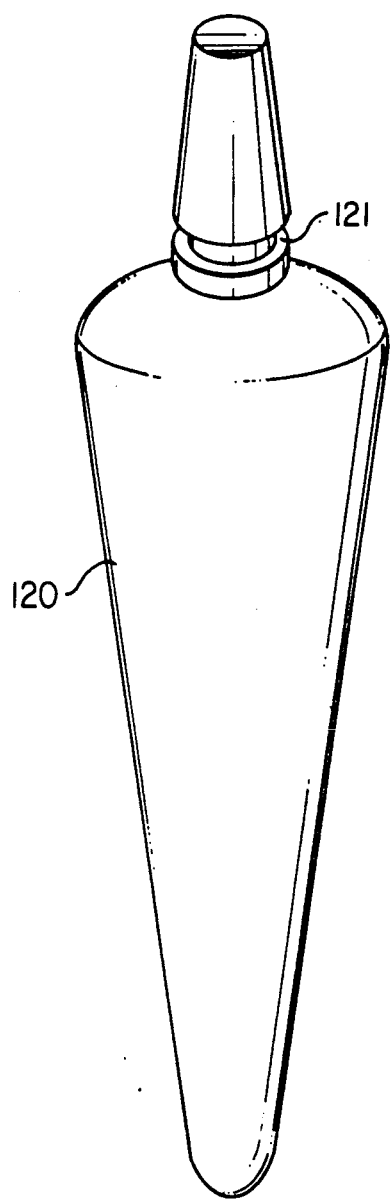
FIG. 22 depicts another form of prosthesis having a pair of indentations.

Neck region 42 is generally cylindrical in shape, although many detachable head prostheses include necks whose cross-sections are generally circular but characterized by gradually decreasing diameters from the distal to the proximal portions (FIG. 22). Moreover, many commercially available detachable and fixed head prostheses include the lower neck regions 43 that are not completely circular in cross section and may have irregularities as enlargements, projections, indentations or flattening of one or several surfaces as shown at 44.

One of the objectives of the device described in U.S. Pat. No. 4,357,716 and the improved device described herein is to hold the stem in the femoral canal in an exacting position of depth, rotation and angulation while the cement is being packed or pressurized. A device, such as described herein, when pinned to the femur is not thereafter changed in position nor is the femoral stem prosthesis; whereas when the cement is packed in the canal and about the stem prosthesis by the surgeons thumb or finger there is some motion of the stem and furthermore some centering devices which may be used on the stem and in the canal may also move to a variable degree. Furthermore, the use of the improved device described herein eliminates the need for cementing centering devices in the femoral canal. The additional use of a retaining unit with the device described herein utilizes the irregularities at or near the base of the neck or may utilize unpolished areas of or near the base of the neck for accurate and definitive positioning of the femoral stem; and when such a device is used with any presently available prosthetic stems, the device will protect the polished highly machined neck.

Figure 8:
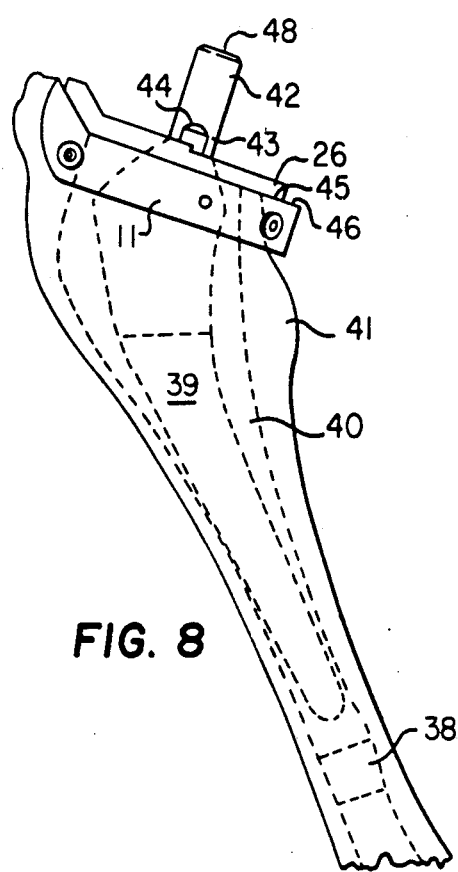
FIG. 8 is a view similar to that of FIG. 7 but additionally including a positioning and sealing member.
Figure 9:
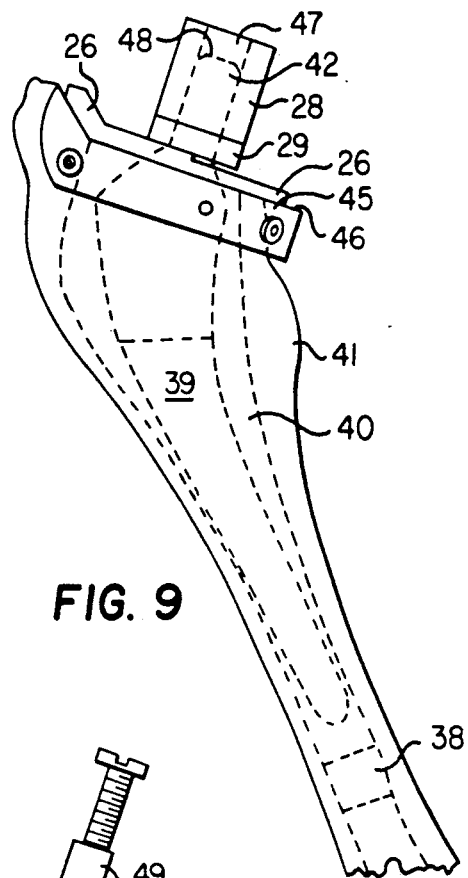
FIG. 9 is a view similar to that of FIG. 8 but additionally including a collar-like member which provides protection for the neck of a detached head prosthesis and which additionally provides improved holding and an increased range of adjustability.

FIG. 8 is similar to FIG. 7 except for the addition of sealer member 26, which has been positioned so that its lower extremity extends to the upper surface 46 of base guide 11 and contacts the upper surface of the resected femur; and FIG. 9 additionally shows adjustment unit 28 and U-shaped guide or holding unit 29 in position upon neck regions 42 and 43.

Considerable improvement in the ease of assembly of the equipment can be obtained by the use of silicone type of adhesive or the like applied to a portion of the interior superior surface of the separator sealer. Thereafter, this portion of the separator sealer is pressed to the interior inferior surface of the ceiling itself. The adhesive is then permitted to dry and the apparatus is then sterilized using known techniques such as gaseous type of sterilization. However, as will be evident to those skilled in the art, radiation sterilization techniques may also be employed.

Figure 10:
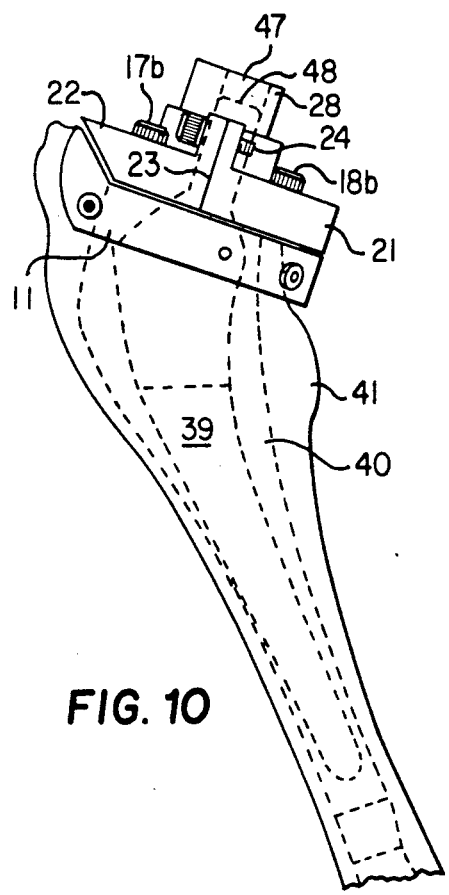
FIG. 10 is a view similar to that of FIG. 9 except showing a ceiling member atop the remaining components.

FIG. 10 shows the remaining parts of assembly 10 positioned atop the parts depicted in FIG. 9. Thus, FIG. 10 shows ceiling halves 21 and 22 in position and assembled by virtue of assembly bolts 17b, 18b and 24; there are contra lateral bolts to 17b, 18b and 24 as shown in FIG. 1. In addition, it will be observed that adjustment ring 28 projects upwardly above the upper surface of ceiling halves 21 and 22 and that it contains recess 47 which is dimensioned sufficiently to provide adequate protection for the upper surface 48 of neck region 42.

Figure 11:
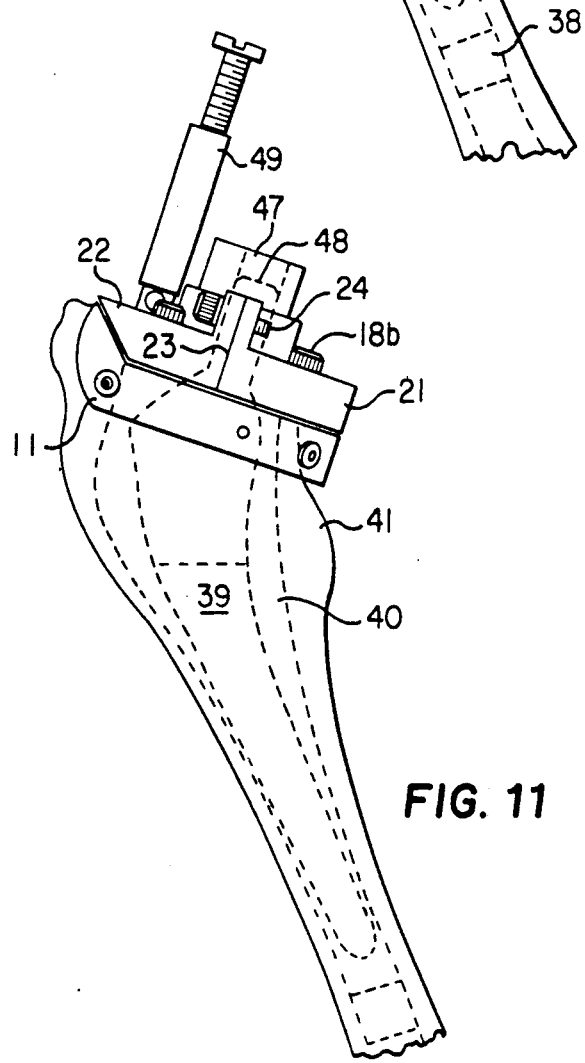
FIG. 11 is a view similar to that of FIG. 10 but additionally showing a portion of the cement injection attachment in position for use.

FIG. 11 is similar to FIG. 10 except for the addition of cementing attachment 49 which is threaded into aperture 31 (FIG. 1). As mentioned above, the cementing attachments are disclosed in the above-identified co-pending application to which reference is herein made.

Figure 12:
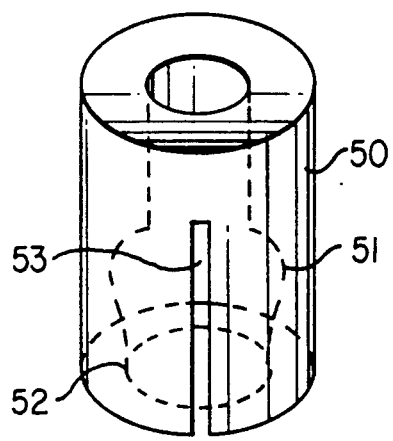
FIG. 12 depicts one of the adjustable collar-like devices with a partial slit according to the inventive concepts hereof.
Figure 13:
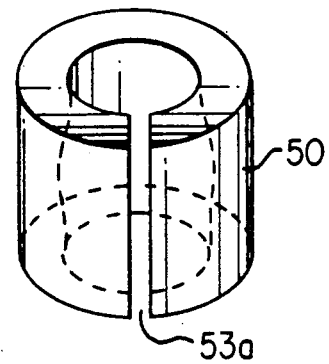
FIG. 13 depicts a shorter form of the collar-like device with a full vertical slit.
Figure 14:
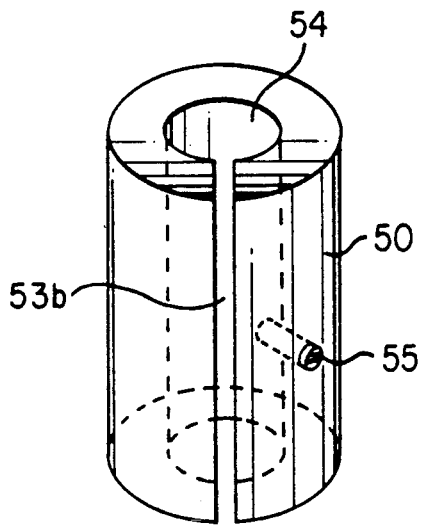
FIG. 14 depicts yet another form of collar-like device with a full vertical slit and including provision for a set screw to hold a prosthesis securely therewithin.

FIGS. 12, 13 and 14 show alternate geometries of holding units adapted to fit different prosthesis neck shapes. Each of these is represented by retaining holding unit 29 shown in earlier figures.

FIG. 12 illustrates one form of retaining unit 50 (similar in function to holding unit 29 in the foregoing figures). Such holding unit 50 is seen to be adapted for mounting on a prosthesis which has a neck with a lower bulbous shape 51. As will be observed from reference to FIG. 12, the maximum diameter of the bulbous part 51 is significantly greater than the diameter at lower portion 52. Accordingly, and in order to provide for mounting, a vertical slit 53 is provided so as to facilitate temporary expansion of the lower part of holding unit 50 while it is being pressed onto the prosthesis neck.

Although mounting holding units onto prostheses necks could be facilitated by employing more resilient (stretchable) material, it has been found that such holding units with greater resiliency do not provide as secure positioning once the holding unit is surrounded by ceiling halves 21 and 22 (FIG. 1). Accordingly, it has been found that the utilization of less resilient material coupled with the provision of a slit such as slit 53 provides improved overall performance.

FIG. 13 depicts a shorter holding unit 50 adapted for mounting on a prosthesis neck of somewhat different geometry. It also (and possibly in further shortened form) is adapted for fitting on the neck of a fixed head prosthesis. Thus, reference to FIG. 13 discloses that holding unit 50 is (or may be) somewhat shorter in vertical dimension than that of FIG. 12 and may include a vertical slit 53a extending the entire vertical dimension of the collar.

FIG. 14 depicts a holding unit 50 having a cylindrical apperture 54 of uniform diameter extending entirely therethrough. In order to retain the desired position of the holding unit on the prosthesis stem neck, set screw 55 is provided to extend transversely through the wall of the holding unit from the exterior to the interior thereof. This set screw may be tightened appropriately to provide sufficient friction to keep the holding unit in place.

As will be evident to those skilled in the art, the selection of the position of set screw 55 and the material of which it is made are to be selected in accordance with the locations on the prosthesis stem neck of suitable engaging surfaces. As mentioned above, the upper portions of the necks of detachable head prostheses are usually highly machined to mirror surface, and it is important that such surfaces be unmarred. Accordingly, where such surfaces extend downwardly entirely through the neck of the prosthesis stem, it may be necessary to employ a set screw 55 made of relatively soft material that will not scratch or unduly mar the mating surface. However, in other constructions, the lower part of the prosthesis stem neck may be in significantly more roughened condition and adapted for mating engagement with a set screw made of harsher material. In any event, through the efficacious employment of a suitable set screw and the utilization of a holding unit having a slit 53b, the principles of the invention hereof may be employed with prostheses having highly polished cylindrically shaped necks.

Figure 15:
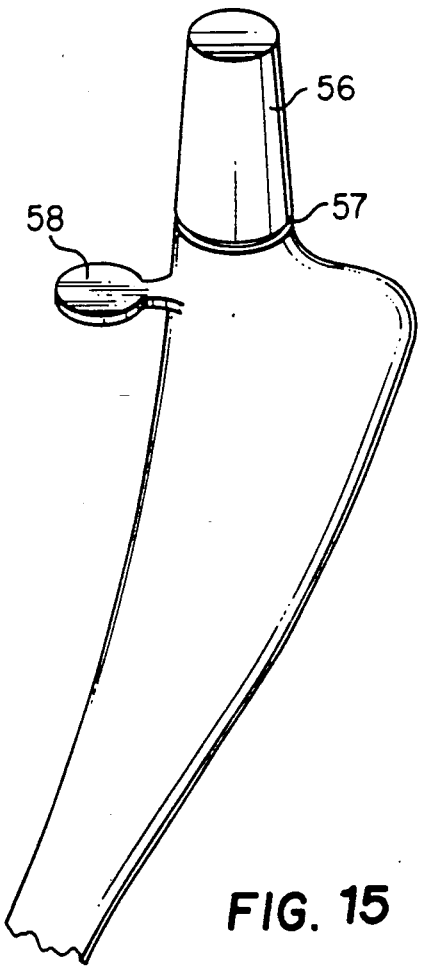
FIG. 15 depicts the geometrical shape of a typical prosthesis with the removable head removed.

FIG. 15 depicts a removable head prosthesis stem having a tapered neck 56 and an indentation 57 near the base thereof. Also shown as part of the prosthesis stem of FIG. 15 is projection 58 and is universally termed a collar which helps prevent the femoral stem prosthesis from migrating too far down the shaft; in some instances, an additional function may be to transfer some of the patient's weight to a part of the superior cut surface of the femur.

Figure 16:
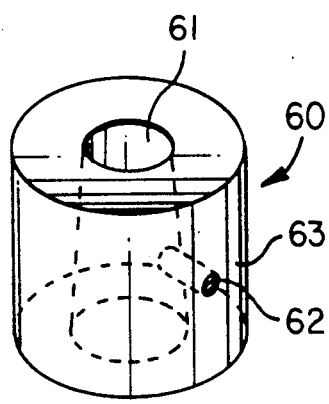
FIG. 16 shows a collar-like device with a tapered interior aperture extending therethrough and including a passageway adapted for a securing screw or bolt.

In FIG. 16, there is shown a holding unit adapted for use with the tapered neck prosthesis stem of FIG. 15. According to FIG. 16, there is provided a holding unit 60 having a frustoconical aperture 61 extending therethrough. Aperture 61 is adapted to conform to the taper of tapered neck 56 of FIG. 15. Since, as is well known, tapered sleeves or collars tend to disassociate themselves from a mating member unless some special measures are employed to retain it in place, passageway 62 (which may or may not be threaded) is provided through the wall 63 so as to accommodate a fastening screw or bolt (not shown).

Figure 17:
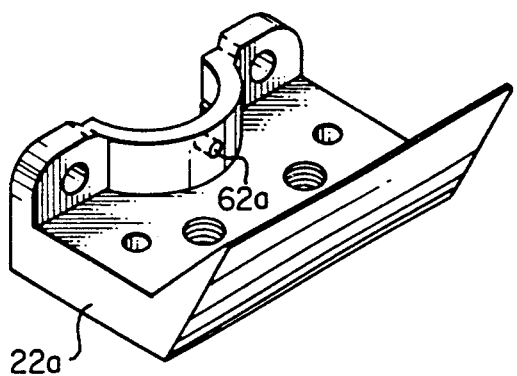
FIG. 17 depicts one portion of an alternative associated ceiling member which is especially adapted for cooperation with the collar-like member of FIG. 16.

If aperture 62 is unthreaded, a means of engaging the aforementioned bolt or screw can be provided in an adjacent portion of the ceiling 22. This is illustrated in FIG. 17 in which an alternate form of ceiling half 22a is depicted. As will be evident from reference to FIG. 17, an aperture 62a is provided and is positioned so as to be in registration with aperture 62 of holding unit 60 when the parts are assembled. It will be thus evidence threads could be provided in aperture 62a and that aperture 62 could be left unthreaded, or conversely, threads could be provided within aperture 62 and aperture 62a could be unthreaded. Moreover, aperture 62a could take the form of a slot or other non-circular geometry as desired. In any event, however, the cooperative geometries of the prosthesis stem of FIG. 15, the engaging holding unit 60 of FIG. 16 and the associated ceiling half 22a of FIG. 17 provide for firm positioning of the prosthesis stem neck within the assembly 10.

In addition to the foregoing, the neck regions of stem prostheses may embody yet other geometrical characteristics. Thus, there may be protrusions, indentations, ridges, and other configurations which depart from the basic geometrical surface shapes of the adjacent regions. Accordingly, the concepts of the invention hereof contemplate corresponding adaptations of the holding units supplied for such configurations so as to exploit them in contributing to the holding characteristics of the holding unit. For example, where a prosthesis stem neck includes an indentation, the position of an aperture such as aperture 62 of FIG. 16 is to be located correspondingly so as to facilitate the utilization of the aforementioned threaded member therethrough to engage such indentation. Moreover, where such a neck region includes an annular recessed portion, a corresponding ring formed integrally as a part of the holding unit 60 or as a separate portion of a split or multi-sectioned holding unit assembly may advantageously be employed to exploit the holding qualities of such an annular recess. If the holding unit is made in two pieces, either or both portions thereof may be compressed by the interior surfaces 33a, 33b, 34a and 34b of the holding unit (FIG. 3) so as to impart the required degree of frictional resistance between the inner surface of the holding unit assembly and the neck of the prosthesis stem to impart the desired holding quality.

Figure 18:
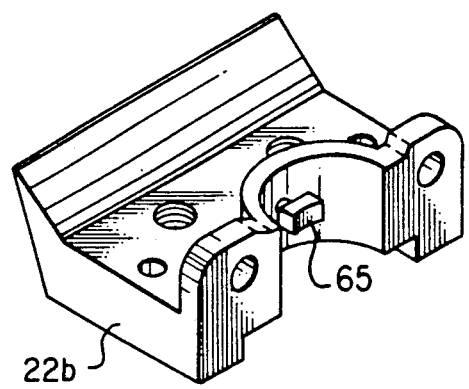
FIG. 18 depicts another alternative form of the structure depicted in FIG. 17.

Now turning to FIG. 18, it will be observed that it depicts an alternative form of ceiling half 22 which is identified with the symbol 22b. Here there is depicted an alternative holding unit holding arrangement which contemplates the utilization of only a sector of a cylindrical holding unit rather than an entire cylindrical shape as in the foregoing descriptions. Such a construction contemplates that the material of which sector 65 is constructed is very smooth and yet exhibits sufficient coefficient of friction to hold the neck of the prosthesis firmly in position when pressure is applied thereto as the ceiling is assembled. Of course, the frictional holding quality of sector 65 may advantageously be supplemented by the frictional engagement of at least some part of the remaining surface of the stem neck with other parts of the interior surfaces of the ceiling. Such contact may be directly with the surfaces (e.g., surfaces 33a, 33b, 34a, 34b) or may be through an interposing transitional medium such as silicone elastomer.

As mentioned above, when a two-part adjustment ring such as that illustrated in FIG. 19 is employed, the process of fitting the adjustment ring around the neck of the prosthesis, properly placing the ceiling and separator sealer can be made easier by the use of a split ring such as that depicted in FIG. 20. The split ring 105 can be snapped around the two parts 90 and 91 after they have been assembled onto the neck of the prosthesis.

Figure 21:
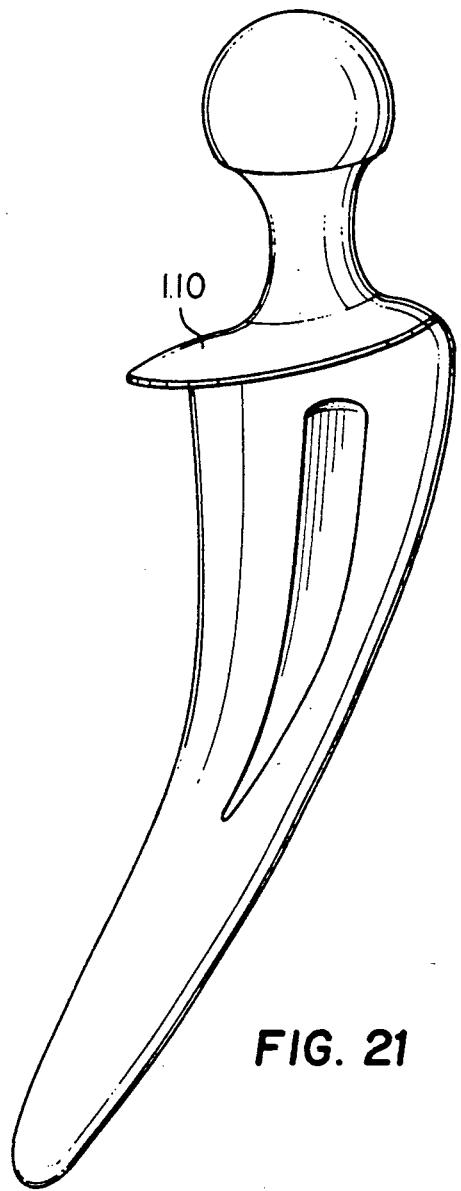
FIG. 21 illustrates a conventional fixed head prosthesis.

FIG. 21 illustrates one form of conventional prosthesis with a fixed head. There, it will be observed, is shown a protrusion 110 extending laterally at a predetermined location below the head.

Now turning to FIG. 22, yet another form of prosthesis is illustrated. There, it will be observed, is a unit having a main body portion 120 at the upper end of which there is a necked-in portion 121 which is adapted for engaging one or more mating engagement members which can be utilized to use the prosthesis in the desired location.

Figure 23:
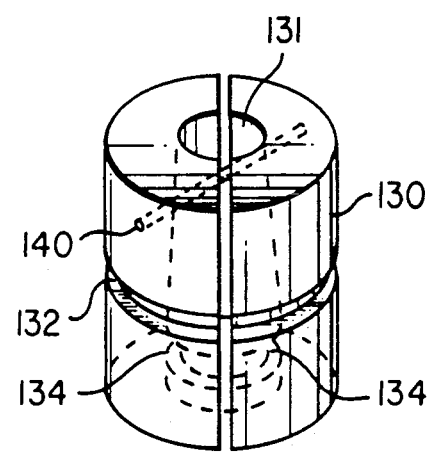
FIG. 23 depicts a collar-like device with slits dividing it into two halves.
Figure 24:
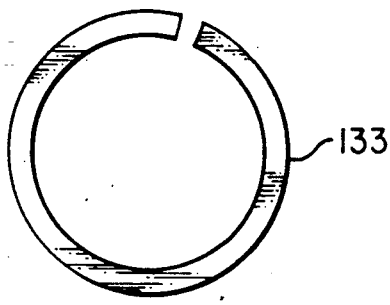
FIG. 24 illustrates a split ring for use with the device of FIG. 23.

A preferred form of adjustment ring/holding unit is shown in FIG. 23 where it will be observed is illustrated a unit similar to that illustrated in FIG. 19 except for the thicker walls 130 and tapered aperture 131. As with the unit of FIG. 19, the unit of FIG. 23 also includes an annular recess 132 which is adapted for mating engagement with the mating snap ring 133 of FIG. 24.

Further reference to the unit of FIG. 23 reveals that aperture 131 does not retain a uniformly tapering geometry therethrough but includes an annular discontinuity 134 which extends about the inner surface of aperture 131 and is adapted for engagement with the annular recess 121 of the prosthesis of FIG. 22. As will be evident to one skilled in the art, the discontinuity 134, when engaged with annular recess 121, is effective to hold the unit of FIG. 23 in place on the neck of the prosthesis of FIG. 22 notwithstanding the tapered geometry of the upper portion thereof. The two halves of the unit may be attached near the proximal end by a small pin or bolt 140. This pin or bolt helps to prevent the two halves from being completely separated and aids in the assembly of the apparatus and femoral stem prosthesis at the time of surgery.

It will now be evident that there has been described herein a prosthesis holding and positioning assembly having substantially improved features. Although the inventive concepts hereof have been illustrated by way of a preferred embodiment, it will be evident to those skilled in the art that other adaptations and modifications may be employed without departing from the spirit and scope of the invention.

I claim:

1. Apparatus for positioning and temporarily holding a femoral stem prosthesis within a prepared canal of a femur while said prosthesis is being affixed within said prepared canal, said prosthesis having a removable head, a neck and stem, said apparatus comprising:
   a. base guide means for attachment to said femur adjacent the proximal end thereof;
   b. holding means being a hollow sleeve having wall-defining inner and outer surfaces, said inner surface being configured for mated fitting on said neck of the prosthesis, said holding means having a radial aperture extending through said wall between said outer and inner surfaces, said radial aperture being adapted for receiving a fastening member therein for fastening said holding means to the neck; and
   c. ceiling means for attachment to said base means, said ceiling means including retaining means for cooperatively engaging said holding means for positioning and temporarily retaining said holding means in a predetermined position with respect to the ceiling means, thereby to position and retain the prosthesis stem in a predetermined position while said prosthesis is being affixed within the prepared canal, said retaining means comprising a fastening screw.

2. Apparatus for positioning and temporarily holding a femoral stem prosthesis within a prepared canal of a femur while said prosthesis is being affixed within said repaired canal, said prosthesis having a removable head, a neck and stem, said apparatus comprising:
   a. base guide means for attachment to said femur adjacent the proximal end thereof;
   b. holding means being a hollow sleeve having wall defining inner and outer surfaces, said inner surface being configured for mated fitting on said neck of the prosthesis, said holding means having a radial aperture extending through said wall between said outer and inner surfaces, said radial aperture being adapted for receiving a fastening member therein for fastening said holding means to the neck,
   c. ceiling means for attachment to said base means, said ceiling means including retaining means for cooperatively engaging said holding means for positioning and temporarily retaining said holding means in a predetermined position with respect to the ceiling means, thereby to position and retain the prosthesis stem in a predetermined position while said prosthesis is being affixed within the prepared canal.

3. Apparatus for positioning and temporarily holding a femoral stem prosthesis within a prepared canal of a femur while said prosthesis is being affixed within said prepared canal, said prosthesis having a removable head, a neck and stem, said apparatus comprising:

a. base guide means for attachment to said femur adjacent the proximal end thereof;

b. holding means being a hollow sleeve having wall-defining inner and outer surfaces, said inner surface being configured for mated fitting on said neck of the prosthesis, said holding means having a first radial aperture extending through said wall between said outer and inner surfaces, said radial aperture being adapted for receiving a fastening member therein for fastening said holding means to the neck; and c. ceiling means for attachment to said base means; said ceiling means including retaining means for cooperatively engaging said holding means for positioning and temporarily retaining said holding means in a predetermined position with respect to the ceiling means, thereby to position and retain the prosthesis stem in a predetermined position while said prosthesis is being affixed within the prepared canal, said retaining means comprising a second radial aperture therethrough in axial alignment with said first radial aperture, each of said radial apertures being adapted for receiving a fastening screw.

* * * * *